(12) United States Patent
Richard

(10) Patent No.: US 9,700,577 B2
(45) Date of Patent: *Jul. 11, 2017

(54) MULTI-COMPONENT PARTICLES FOR INJECTION AND PROCESSES FOR FORMING THE SAME

(71) Applicant: Boston Scientific Scimed, Inc., Maple Grove, MN (US)

(72) Inventor: Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/828,295

(22) Filed: Aug. 17, 2015

(65) Prior Publication Data

US 2015/0352146 A1 Dec. 10, 2015

Related U.S. Application Data

(63) Continuation of application No. 12/245,365, filed on Oct. 3, 2008, now Pat. No. 9,107,828.

(60) Provisional application No. 60/997,848, filed on Oct. 5, 2007.

(51) Int. Cl.
*A61K 9/16* (2006.01)
*A61K 31/78* (2006.01)
*A61K 9/00* (2006.01)
*A61K 31/717* (2006.01)
*A61K 31/765* (2006.01)
*A61K 31/785* (2006.01)

(52) U.S. Cl.
CPC ............ *A61K 31/78* (2013.01); *A61K 9/0019* (2013.01); *A61K 9/0024* (2013.01); *A61K 9/16* (2013.01); *A61K 9/1635* (2013.01); *A61K 9/1641* (2013.01); *A61K 31/717* (2013.01); *A61K 31/765* (2013.01); *A61K 31/785* (2013.01)

(58) Field of Classification Search
None
See application file for complete search history.

(56) References Cited

U.S. PATENT DOCUMENTS

| | | | | |
|---|---|---|---|---|
| 5,543,158 | A | * 8/1996 | Gref | A61K 9/0019 424/451 |
| 9,107,828 | B2 | * 8/2015 | Richard | A61K 9/0019 |
| 2005/0175709 | A1 | * 8/2005 | Baty, III | A61B 17/12022 424/489 |
| 2007/0059363 | A1 | * 3/2007 | Lee | A61K 38/24 424/468 |
| 2007/0237800 | A1 | * 10/2007 | Lahann | A61K 9/1694 424/422 |
| 2007/0264481 | A1 | * 11/2007 | DeSimone | A61K 9/5138 428/220 |

OTHER PUBLICATIONS

T Nisisako, T Torii, T Higuchi. "Novel microreactors for functional polymer beads." Chemical Engineering Journal, vol. 101, 2004, pp. 23-29.*

* cited by examiner

*Primary Examiner* — Isaac Shomer

(57) ABSTRACT

In accordance with one aspect of the invention, novel compositions containing injectable particles are provided in which the injectable particles contain at least two polymeric components that differ in composition from one another (e.g., because at least one polymeric component contains a polymer that is not present in another polymeric component).

20 Claims, 1 Drawing Sheet

MULTI-COMPONENT PARTICLES FOR INJECTION AND PROCESSES FOR FORMING THE SAME

STATEMENT OF RELATED APPLICATIONS

This application is a continuation of U.S. patent application Ser. No. 12/245,365, filed Oct. 3, 2008, entitled "Multi-Component Particles For Injection And Processes For Forming The Same", which claims the benefit of U.S. Provisional Patent Application Ser. No. 60/997,848, filed Oct. 5, 2007, entitled "Multi-Component Particles For Injection And Processes For Forming The Same", each of which is incorporated by reference herein in its entirety.

FIELD OF THE INVENTION

The invention relates to multi-component particles for injection and to processes for forming the same.

BACKGROUND OF THE INVENTION

Many clinical situations benefit from therapeutic regulation of the vascular, lymphatic or duct systems by restricting the flow of body fluid or secretions. The technique of embolization involves the therapeutic introduction of particles into the circulation to occlude vessels, for example, so as to either arrest or prevent hemorrhaging or to cut off blood flow to a structure or organ. Permanent or temporary occlusion of blood vessels is desirable for managing various diseases, disorders and conditions.

In a typical embolization procedure, local anesthesia is first given over a common artery. The artery is then percutaneously punctured and a catheter is inserted and fluoroscopically guided into the area of interest. An angiogram is then performed by injecting contrast agent through the catheter. An embolic agent is then deposited through the catheter. The embolic agent is chosen, for example, based on the size of the vessel to be occluded, the desired duration of occlusion, and/or the type of abnormality to be treated. A follow-up angiogram is usually performed to determine the specificity and completeness of the arterial occlusion.

Various polymer-based microspheres are currently employed to embolize blood vessels. These microspheres are usually introduced to the location of the intended embolization through microcatheters. Current commercially available embolic microspheres are composed of biostable polymers. The materials that have been most commonly used commercially include polyvinyl alcohol (PVA), acetalized PVA (e.g., Contour SE™ embolic agent, Boston Scientific, Natick, Mass., USA) and crosslinked acrylic hydrogels (e.g., Embospheres®, Biosphere Medical, Rockland, Mass., USA). Similar devices have been used in chemoembolization to increase the residence time of the therapeutic after delivery. In one specific instance, a therapeutic agent (doxorubicin) has been directly added to polyvinyl alcohol hydrogel microspheres such that it can be released locally after delivery (e.g., DC Bead™ drug delivery chemoembolization system, Biocompatibles International plc, Farnham, Surrey, UK).

Current commercial processes for the production of embolic particles include emulsion polymerization as well as emulsification of preformed polymers and encapsulation technologies. For example microspheres of PVA can be prepared by dispersing an aqueous PVA solution in an immiscible solvent and crosslinking it with a suitable material such as an aldehyde (e.g., formaldehyde or gluteraldehyde). Another example of microsphere preparation involves dropping an aqueous solution of PVA and sodium alginate into a calcium chloride bath, followed by reaction with an aldehyde to crosslink the PVA. See, e.g., Pub. No. US 2003/0185895 to Lanphere et al.

It is also known to use polymer-based microspheres as augmentative materials for aesthetic improvement, including improvement of skin contour. Furthermore, polymer-based microspheres have also been used as augmentative materials in the treatment of various diseases, disorders and conditions, including urinary incontinence, vesicourethral reflux, fecal incontinence, intrinsic sphincter deficiency (ISD) and gastro-esophageal reflux disease. For instance, a common method for treating patients with urinary incontinence is via periurethral or transperineal injection of a bulking agent that contains polymer-based microspheres. In this regard, methods of injecting bulking agents commonly require the placement of a needle at a suitable treatment region, for example, periurethrally or transperineally. The bulking agent is injected into a plurality of locations, assisted by visual aids, causing the urethral lining to coapt. In some cases additional applications of bulking agent are required.

SUMMARY OF THE INVENTION

In accordance with one aspect of the invention, novel particulate compositions containing injectable particles are provided in which the injectable particles contain at least two polymeric components that differ in composition from one another.

These and various additional aspects, embodiments and advantages of the present invention will become immediately apparent to those of ordinary skill in the art upon review of the Detailed Description and any claims to follow.

DETAILED DESCRIPTION

In accordance with one aspect of the invention, particulate compositions containing injectable particles are provided in which the injectable particles contain at least two polymeric components that differ in composition from one another.

Polymeric components that differ in composition are commonly thermodynamically incompatible with one another. The thermodynamic incompatibility causes phase separation between the polymeric components of the particles, resulting in a heterogeneous particle with regions that are chemically different from each other. This allows for the engineering of particles with regions which can be used to differentially load and/or deliver one or more therapeutic agents as well as the ability to modulate therapeutic agent delivery.

Figure 1:
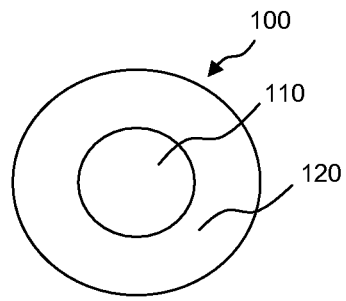
FIG. 1 is a schematic illustration of a particle in accordance with an embodiment of the invention in which one component is in the form of a spherical core and another component is in the form of a shell.
Figure 2:
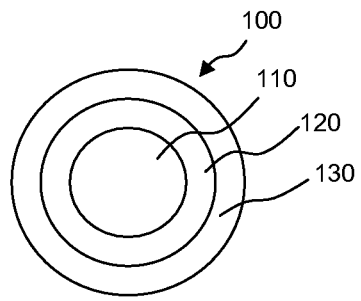
FIG. 2 is a schematic illustration of a particle in accordance with an embodiment of the invention in which one component is in the form of a spherical core and other components are in the form of multiple concentric shells.

The multiple components may be spherically symmetric with respect to one another. For example, as shown in FIG. 1, the particle 100 may contain one component 110 in the form of a spherical core and another component 120 in the form of a shell. As another example, as shown in FIG. 2, the particle 100 may contain one component 110 in the form of a spherical core and other components 120,130 in the form of multiple concentric shells.

Figure 3:
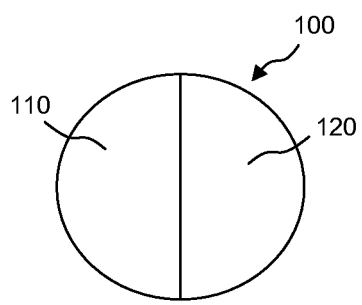
FIG. 3 is a schematic illustration of a particle in accordance with an embodiment of the invention, which contains first and second side-by-side components that are generally hemispherical in shape.
Figure 4:
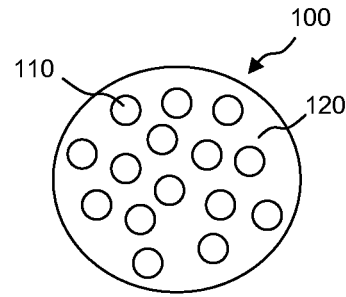
FIG. 4 is a schematic illustration of a particle in accordance with an embodiment of the invention, which includes multiple spherical cores of a first polymeric component distributed in a single continuous phase of a second component.
Figure 5:
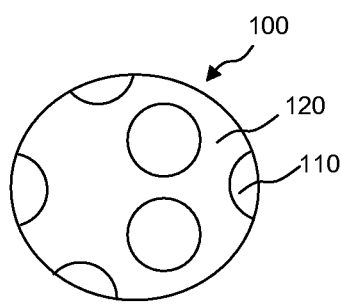
FIG. 5 is a schematic illustration of a particle in accordance with an embodiment of the invention, which includes multiple regions of a first polymeric component distributed on a surface of a single continuous phase of a second component.

In other embodiments, the multiple components are not spherically symmetric with respect to one another such that the particles have one or more planes of asymmetry that pass through their centers. For example, referring to FIG. 3 the particles 100 may contain first and second side-by-side components 110,120 that are generally hemispherical in shape. With reference to FIG. 4, the particles may contain multiple spherical cores of a first polymeric component 110 within a spherical particle 100 that comprises a single continuous phase of a second component 120. With reference to FIG. 5, the particles may contain multiple regions of a first polymeric component 110 distributed on a surface of a spherical particle 100 that comprises a single continuous phase of a second component 120, and so forth.

The injectable particles of the invention may take on a wide variety of shapes. In certain embodiments, they are spherical, for example, having the form of a perfect (to the eye) sphere or the form of a near-perfect sphere such as a prolate spheroid (a slightly elongated sphere) or an oblate spheroid (a slightly flattened sphere). In some embodiments, they may contain incompletely merged spheroids (e.g., of a "snowman" shape). More typically, the particles are substantially spherical. The injectable particles of the invention can be of various sizes, with typical longest linear cross-sectional dimensions (e.g., for a sphere, the diameter) ranging, for example, from 150 to 250 to 500 to 750 to 1000 to 1500 to 2000 to 2500 to 5000 microns (μm).

By a "polymeric component" is meant a distinct polymer-containing phase within the injectable particle, which may contain, for example, from 50 wt % or less to 75 wt % to 90 wt % to 95 wt % to 97.5 wt % to 99 wt % or more polymers as well as other optional agents such a therapeutic agents, among others.

As used herein, "polymers" are molecules that contain multiple copies of one or more types of constitutional units, commonly referred to as monomers. The number of monomers/constitutional units within a given polymer may vary widely, ranging, for example, from 5 to 10 to 25 to 50 to 100 to 1000 to 10,000 or more constitutional units. As used herein, the term "monomers" may refer to the free monomers and those that are incorporated into polymers, with the distinction being clear from the context in which the term is used. Polymers for use in the polymeric regions of the present invention can have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains, such as graft polymers), dendritic architectures (e.g., arborescent and hyperbranched polymers), and networked architectures (e.g., crosslinked polymers), among others.

Polymers containing a single type of monomer are called homopolymers, whereas polymers containing two or more types of monomers are referred to as copolymers. The two or more types of monomers within a given copolymer may be present in any of a variety of distributions including random, statistical, gradient and periodic (e.g., alternating) distributions, among others. One particular type of copolymer is a "block copolymer," which is a copolymer that contains two or more polymer chains of different composition, which chains may be selected from homopolymer chains and copolymer chains (e.g., random, statistical, gradient or periodic copolymer chains). As used herein, a polymer "chain" is a linear assembly of monomers and may correspond to an entire polymer or to a portion of a polymer.

Specific polymers for use in forming polymeric components in accordance with the invention may be selected, for example, from one or more suitable members of the following, among others: polycarboxylic acid homopolymers and copolymers including polyacrylic acid, polymethacrylic acid, ethylene-methacrylic acid copolymers and ethylene-acrylic acid copolymers, where some of the acid groups can be neutralized with either zinc or sodium ions (commonly known as ionomers); acetal homopolymers and copolymers; acrylate and methacrylate homopolymers and copolymers (e.g., n-butyl methacrylate); cellulosic homopolymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene homopolymers and copolymers; polyimide homopolymers and copolymers such as polyether block imides, polyamidimides, polyesterimides, and polyetherimides; polysulfone homopolymers and copolymers including polyarylsulfones and polyethersulfones; polyamide homopolymers and copolymers including nylon 6,6, nylon 12, polycaprolactams, polyacrylamides and polyether block amides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); homopolymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-alkylene copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene (SIBS) block copolymers such as those disclosed in U.S. Pat. No. 6,545,097 to Pinchuk), poly[(styrene-co-p-methylstyrene)-b-isobutylene-b-(styrene-co-p-methylstyrene)] (SMIMS) triblock copolymers described in S. J. Taylor et al., Polymer 45 (2004) 4719-4730; polyphosphonate homopolymers and copolymers; polysulfonate homopolymers and copolymers, for example, sulfonated vinyl aromatic polymers and copolymers, including block copolymers having one or more sulfonated poly(vinyl aromatic) blocks and one or more polyalkene blocks, for example, sulfonated polystyrene-polyolefin-polystyrene triblock copolymers such as the sulfonated SEBS copolymers described in U.S. Pat. No. 5,840,387, and sulfonated versions of SIBS and SMIMS, which polymers may be sulfonated, for example, using the processes described in U.S. Pat. No. 5,840,387 and U.S. Pat. No. 5,468,574, among other sulfonated block copolymers; polyvinyl ketones, polyvinylcarbazoles, and polyvinyl esters such as polyvinyl acetates; polybenzimidazoles; polyalkyl oxide homopolymers and copolymers including polyethylene oxides (PEO); polyesters including polyethylene terephthalates and aliphatic polyesters such as homopolymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly (caprolactone) is one specific example); polyether homopolymers and copolymers including polyarylethers such as polyphenylene ethers, polyether ketones, polyether ether ketones; polyphenylene sulfides; polyisocyanates; polyolefin homopolymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated homopolymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone homopolymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; polyamine and polyimine homopolymers and copolymers; biopolymers, for example, polypeptides including anionic polypeptides such as polyglutamate and cationic polypeptides such as polylysine, proteins, polysaccharides, and fatty acids (and esters thereof), including fibrin, fibrinogen, collagen, elastin, chitosan, gelatin, starch, glycosaminoglycans such as hyaluronic acid; as well as further copolymers of the above.

Examples of biodegradable polymers, not necessarily exclusive of those set forth above, may be selected from suitable members of the following, among many others: (a) polyester homopolymers and copolymers such as polyglycolide, poly-L-lactide, poly-D-lactide, poly-D,L-lactide, poly(beta-hydroxybutyrate), poly-D-gluconate, poly-L-gluconate, poly-D,L-gluconate, poly(epsilon-caprolactone), poly(delta-valerolactone), poly(p-dioxanone), poly(trimethylene carbonate), poly(lactide-co-glycolide) (PLGA), poly (lactide-co-delta-valerolactone), poly(lactide-co-epsilon-caprolactone), poly(lactide-co-beta-malic acid), poly (lactide-co-trimethylene carbonate), poly(glycolide-co-trimethylene carbonate), poly(beta-hydroxybutyrate-co-beta-hydroxyvalerate), poly[1,3-bis(p-carboxyphenoxy) propane-co-sebacic acid], and poly(sebacic acid-co-fumaric acid), among others, (b) poly(ortho esters) such as those synthesized by copolymerization of various diketene acetals and diols, among others, (c) polyanhydrides such as poly (adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis(p-carboxyphenoxy) hexane anhydride], among others; and (d) amino-acid-based polymers including tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and tyrosine-, leucine- and lysine-based polyester-amides; specific examples of tyrosine-based polymers include includes polymers that are comprised of a combination of desaminotyrosyl tyrosine hexyl ester, desaminotyrosyl tyrosine, and various di-acids, for example, succinic acid and adipic acid, more specifically tyrosine-derived ester-amides such as the TyRx 2,2 family of polymers, available from TyRx Pharma, Inc., Monmouth Junction, N.J., USA, among others.

Hence, the injectable particles of the invention may contain the following, among many other possibilities: (a) one or more biostable polymeric components that contain at least one biostable polymer, including, for example, hydrogel and/or non-hydrogel biostable polymeric components, which component(s) may or may not contain one or more therapeutic agents, (b) one or more biodegradable polymeric components that contain at least one biodegradable polymers, which component(s) may or may not contain one or more therapeutic agents, (c) one or more polymeric components that contain an admixture of biostable and biodegradable polymers, which component(s) may or may not contain one or more therapeutic agents, and/or (d) one or more polymeric components that contain a biostable or biodegradable ionic polymer (e.g., to provide electro-repulsive or electro-attractive forces between the particles, to promote or retard delivery of a therapeutic agent, if present, etc.).

As used herein a hydrogel is a polymeric material that absorbs water in an amount that measurably changes its dimensions. For example, a hydrogel containing particle in accordance with the invention may undergo swelling in water such that its longest linear cross-sectional dimension (e.g., for a sphere, the diameter) increases by 5% or less to 10% to 15% to 20% to 25% or more.

As used herein an aqueous fluid (e.g., a solution, suspension, etc.) is one which contains water, typically from 50 wt % or less to 75 wt % to 90 wt % to 95 wt % to 97.5 wt % to 99 wt % or more water.

As used herein, a polymer is biodegradable if it undergoes bond cleavage along the polymer backbone in vivo, regardless of the mechanism of bond cleavage (e.g., enzymatic breakdown, hydrolysis, oxidation, etc.).

As indicated above, in certain embodiments, the particulate compositions of the present invention include one or more therapeutic agents. The agents may be provided within the particles themselves or as part of an aqueous phase within which the particles are suspended. Concentrations will vary widely depending on a number of factors including the disease, disorder or condition being treated, the potency of the therapeutic agent, and the volume of particulate composition that is ultimately injected into the subject, among other factors, and can be determined by those of ordinary skill in the art. Typical therapeutic agent concentration ranges are, for example, from about 0.1 to 50 wt % of the injected composition, more typically about 1 to 10 wt %, among other possibilities.

Examples of therapeutic agents to be used with embolic compositions include toxins (e.g., a ricin toxin, a radionuclide, or any other agent able to kill undesirable cells such as those making up cancers and other tumors such as uterine fibroids) and agents that arrest growth of undesirable cells.

Some specific examples of therapeutic agents for embolic compositions may be selected from suitable members of the following: antineoplastic/antiproliferative/anti-miotic agents including antimetabolites such as folic acid analogs/antagonists (e.g., methotrexate, etc.), purine analogs (e.g., 6-mercaptopurine, thioguanine, cladribine, which is a chlorinated purine nucleoside analog, etc.) and pyrimidine analogs (e.g., cytarabine, fluorouracil, etc.), alkaloids including taxanes (e.g., paclitaxel, docetaxel, etc.), alkylating agents such as alkyl sulfonates, nitrogen mustards (e.g., cyclophosphamide, ifosfamide, etc.), nitrosoureas, ethylenimines and methylmelamines, other aklyating agents (e.g., dacarbazine, etc.), antibiotics and analogs (e.g., daunorubicin, doxorubicin, idarubicin, mitomycin, bleomycins, plicamycin, etc.), platinum complexes (e.g., cisplatin, carboplatin, etc.), antineoplastic enzymes (e.g., asparaginase, etc.), agents affecting microtubule dynamics (e.g., vinblastine, vincristine, colchicine, Epo D, epothilone), caspase activators, proteasome inhibitors, angiogenesis inhibitors (e.g., statins such as endostatin, cerivastatin and angiostatin, squalamine, etc.), rapamycin (sirolimus) and its analogs (e.g., everolimus, tacrolimus, zotarolimus, etc.), etoposides, as well as many others (e.g., hydroxyurea, flavopiridol, procarbizine, mitoxantrone, campothecin, etc.), various pharmaceutically acceptable salts and esters of the foregoing, and combinations of the foregoing, among other agents.

Further agents suitable for treatment of uterine fibroids, many of which are suitable for the treatment of tumors other than fibroids, are listed in Pub. No. US 2006/0251581 to McIntyre et al., and include chemical ablation agents (materials whose inclusion in the formulations of the present invention in effective amounts results in necrosis or shrinkage of nearby tissue upon injection) including osmotic-stress-generating agents (e.g., salts, etc.), basic agents (e.g., sodium hydroxide, potassium hydroxide, etc.), acidic agents (e.g., acetic acid, formic acid, etc.), enzymes (e.g., collagenase, hyaluronidase, pronase, papain, etc.), free-radical generating agents (e.g., hydrogen peroxide, potassium peroxide, etc.), other oxidizing agents (e.g., sodium hypochlorite, etc.), tissue fixing agents (e.g., formaldehyde, acetaldehyde, glutaraldehyde, etc.), coagulants (e.g., gengpin, etc.), non-steroidal anti-inflammatory drugs, contraceptives (e.g., desogestrel, ethinyl estradiol, ethynodiol, ethynodiol diacetate, gestodene, lynestrenol, levonorgestrel, mestranol, medroxyprogesterone, norethindrone, norethynodrel, norgestimate, norgestrel, etc.), GnRH agonists (e.g, buserelin, cetorelix, decapeptyl, deslorelin, dioxalan derivatives, eulexin, ganirelix, gonadorelin hydrochloride, goserelin, goserelin acetate, histrelin, histrelin acetate, leuprolide, leuprolide acetate, leuprorelin, lutrelin, nafarelin, meterelin, triptorelin, etc.), antiprogestogens (e.g., mifepristone, etc.), selective progesterone receptor modulators (SPRMs) (e.g., asoprisnil, etc.), various pharmaceutically acceptable salts and esters of the foregoing, and combinations of the foregoing, among other agents.

For tissue bulking applications (e.g., urethral bulking, cosmetic bulking, etc.), specific beneficial therapeutic agents include those that promote collagen production, including proinflammatory agents and sclerosing agents such as those listed in Pub. No. US 2006/0251697 to Li et al.

Suitable proinflammatory agents can be selected, for example, from suitable endotoxins, cytokines, chemokines, prostaglandins, lipid mediators, and other mitogens. Specific examples of known proinflammatory agents from which suitable proinflammatory agents can be selected include the following: growth factors such as platelet derived growth factor (PDGF), fibroblast growth factor (FGF), transforming growth factor (such as TGF-alpha and TGF-beta), epidermal growth factor (EGF), insulinlike growth factor (IGF), interleukins such as IL-1-(alpha or beta), IL-8, IL-4, IL6, IL-10 and IL-13, tumor necrosis factor (TNF) such as TNF-alpha, interferons such as INF-gamma, macrophage inflammatory protein-2 (MIP-2), leukotrienes such as leukotriene B4 (LTB4), granulocyte macrophage-colony stimulating factor (GM-CSF), cyclooxygenase-1, cyclooxygenase-2, macrophage chemotactic protein (MCP), inducible nitric oxide synthetase, macrophage inflammatory protein, tissue factor, phosphotyrosine phosphates, N-formyl peptides such as formyl-Met-Leu-Phe (fMLP), second mitochondria-derived activator of caspase (sMAC), activated complement fragments (C5a, C3a), phorbol ester (TPA), superoxide, hydrogen peroxide, zymosan, bacterial lipopolysaccharide, chitin, imiquimod, carrageenan, various pharmaceutically acceptable salts and esters of the foregoing, and combinations of the foregoing, among other agents.

Suitable sclerosing agents for the practice of the invention can be selected, for example, from the following (which list is not necessarily exclusive of the proinflammatory list set forth above): inorganic materials such as talc, aluminum hydroxide (e.g., in slurry form), sodium hydroxide, silver nitrate and sodium chloride, as well as organic compounds, including alcohols such as ethanol (e.g., 50% to absolute), acetic acid, trifluoroacetic acid, formaldehyde, dextrose, polyethylene glycol ethers (e.g., polidocanol, also known as laureth 9, polyethylene glycol (9) monododecyl ether, and hydroxypolyethoxydodecane), tetracycline, oxytetracycline, doxycycline, bleomycin, triamcinolone, minocycline, vincristine, iophendylate, tribenoside, sodium tetradecyl sulfate, sodium morrhuate, diatrizoate meglumine, prolamine diatrizoate, alkyl cyanoacrylates such as N-butyl-2-cyanoactyalte and methyl 2-cyanoacrylate, ethanolamine, ethanolamine oleate, bacterial preparations (e.g., corynebacterium and streptococcal preparations such as picibanil) and mixtures of the same, for instance, TES (mixture of 1% tetradecyl sulfate, 32% ethanol, and 0.3% normal saline) and alcoholic solutions of zein (e.g., Ethibloc, which contains zein, alcohol, oleum papaveris, propylene glycol, and a contrast medium), and ethanol/trifluoroacetic acid mixtures, among others.

Various procedures have associated with them some degree of pain. Thus, in certain embodiments, the injectable particles of the invention contain one or more agents selected from narcotic analgesics, non-narcotic analgesics, local anesthetic agents and other pain management agents.

Examples of narcotic analgesic agents for use in the present invention may be selected from suitable members of the following: codeine, morphine, fentanyl, meperidine, propoxyphene, levorphanol, oxycodone, oxymorphone, hydromorphone, pentazocine, and methadone, among others, as well as combinations and pharmaceutically acceptable salts, esters and other derivatives of the same.

Examples of non-narcotic analgesic agents for use in the present invention may be selected from suitable members of the following: analgesic agents such as acetaminophen, and non-steroidal anti-inflammatory drugs such as aspirin, diflunisal, salsalate, ibuprofen, ketoprofen, naproxen indomethacin, celecoxib, valdecoxib, diclofenac, etodolac, fenoprofen, flurbiprofen, ketorolac, meclofenamate, meloxicam, nabumetone, naproxen, oxaprozin, piroxicam, sulindac, tolmetin, and valdecoxib, among others, as well as combinations and pharmaceutically acceptable salts, esters and other derivatives of the same.

Examples of local anesthetic agents for use in the present invention may be selected from suitable members of the following: benzocaine, cocaine, lidocaine, mepivacaine, and novacaine, among others, as well as combinations and pharmaceutically acceptable salts, esters and other derivatives of the same.

In one specific embodiment, the injectable particles of the invention contain the following polymeric components: (a) a first component comprising a crosslinked hydrophilic polymer (e.g., a hydrogel component) to impart swellability to the particles and (b) a second component, which contains biostable and/or biodegradable polymers, which contains a therapeutic agent, and which releases the therapeutic agent in vivo.

In another specific embodiment, the injectable particles of the invention contain the following polymeric components: (a) a first component, which contains biostable and/or biodegradable polymers, and which has with good tissue affinity or tissue adhesion properties, and (b) a second component, which contains biostable and/or biodegradable polymers, which contains a therapeutic agent, and which releases the therapeutic agent in vivo.

In other specific embodiments, the injectable particles of the invention contain the following polymeric components: (a) a first component, which contains first biostable and/or biodegradable polymers, which contains a first therapeutic agent, and which releases the first therapeutic agent in vivo, and (b) a second component, which contains second biostable and/or biodegradable polymers, which contains a second therapeutic agent, and which releases the second therapeutic agent in vivo. In certain embodiments, the first and second polymers are different and the first and second therapeutic agents are the same, leading to more complex (e.g., bimodal) therapeutic agent delivery profiles. In certain embodiments, the first and second polymers are different and the first and second therapeutic agents are different, allowing, for instance, the release of the first and second therapeutic agents to be independently optimized. For example, it may be desirable to quickly release a first therapeutic agent, for example, a thrombogenic agent such as thrombin for purposes of accelerated clotting and tumor necrosis, and to more slowly release a second therapeutic agent, for example, an antineoplastic/antiproliferative/anti-miotic agent such as doxorubicin for purposes of inhibiting tumor growth.

In other specific embodiments, the injectable particles of the invention contain the following polymeric components: (a) a first component comprising a first ionic biodegradable or biostable polymer, and (b) a second component comprising a second ionic biodegradable or biostable polymer. In certain embodiments, the first and second ionic polymers have the same charge. In certain embodiments, the first and second ionic polymers have the opposite charge. In either case, the charges (and charge densities) may lead to differences in sphere aggregation/dispersion as well as differences in delivery properties (e.g., where a charged or polar therapeutic agent is present in either or both of the components).

In other specific embodiments, the injectable particles of the invention contain the following polymeric components: (a) a first component comprising a first biodegradable or biostable polymer, and (b) a second component comprising a second biodegradable or biostable polymer, wherein the first polymeric component has a density that differs from that of the second component. For example, by adjusting the density of the first and second components, the overall density of the particles may be matched to the density of aqueous phase that suspends the particles (e.g., an injection medium that contains a saline solution that further includes a contrast agent such as Omnipaque™ or Visipaque™, among other possibilities), producing neutral buoyancy for the particles. This may, for instance, improve particle dispersibility prior to delivery.

Injectable particles in accordance with the invention may be formed, for example, by contacting two or more polymer-containing liquid droplets with one another, which droplets are capable of coalescing into a single composite droplet upon contact. The single composite droplet then solidifies to form an injectable particle. Examples of polymer-containing droplets in liquid form include polymer melts, polymer solutions, curable liquid prepolymers (i.e., polymers having a degree of polymerization between that of the monomer or monomers forming the polymer and the final polymer), and so forth. Examples of solidification processes include cooling, solvent removal, thermal cure, and ultraviolet radiation cure, among others.

One specific technique for forming composite particles is described in M. Fialkowski et al., "Self-assembly of polymeric microspheres of complex internal structures," *Nature Materials*, Vol. 4, January 2005, pp. 93-97. In this article, multicomponent polymeric microspheres having various internal geometries are produced by a process in which relatively hydrophobic droplets of liquid prepolymers (i.e., polydimethylsiloxane, polyurethane and epoxy prepolymers) having a relatively low interfacial energy with respect to one another are first printed onto a water-soluble hydrogel, where the droplets are allowed to spread and coalesce into composite "patches." It is reported that the density of the prepolymer droplets can differ by as much as 10%. These patches are then immersed in a liquid having a density that is equal to the overall density of the patches (and "isodense" liquid), which both compensates the force of gravity and which dissolves the gel beneath the patches, whereupon the patches are released from the surface and form spheres whose internal structures are dictated by the arrangement of the droplets previously printed onto the surface. The spheres are then solidified thermally or by ultraviolet radiation.

Using the techniques described in Fialkowski et al., for example, particles containing a polyurethane component and a silicone component, either of which may comprise a therapeutic agent, may be formed.

More broadly, multicomponent polymeric microspheres for use in the present invention may be produced by a process in which relatively hydrophilic (or relatively hydrophobic) liquid polymer droplets having a relatively low interfacial energy with respect to one another such that they are capable of coalescing into a composite droplet, which droplets may or may not contain a therapeutic agent, are first printed onto a water-soluble (or an organic-solvent-soluble) material and the droplets are allowed to spread and coalesce into composite droplets. The composite droplets are then immersed in an isodense aqueous solution (or an isodense hydrophobic organic solution), which dissolves the water-soluble material (or organic-solvent-soluble material), thereby forming spheres which are then solidified, for example, by cooling, solvent removal, thermal curing, or ultraviolet radiation curing, among others.

For example, UV curable liquid prepolymers of polylactic acid, polyglycolic acid, polyethylene glycol, acrylates, and methacrylates are available commercially.

Because prepolymer droplets can be deposited by ink jet or another highly controllable deposition process, the process may be amenable to producing microspheres that contain expensive biologically derived therapeutic agents such as genes, growth factors, and proteins among many others.

The injectable particles of the invention may be stored and transported in dry form. The dry composition may also optionally contain additional agents, for example, one or more of the following among others: (a) tonicity adjusting agents including sugars (e.g., dextrose, lactose, etc.), polyhydric alcohols (e.g., glycerol, propylene glycol, mannitol, sorbitol, etc.) and inorganic salts (e.g., potassium chloride, sodium chloride, etc.), (b) therapeutic agents, for example, selected from those listed above, (c) suspension agents including various surfactants, wetting agents, and polymers (e.g., albumen, PEO, polyvinyl alcohol, block copolymers, etc.), (d) imaging contrast agents (e.g., Omnipaque™, Visipaque™, etc.), and (e) pH adjusting agents including various buffer solutes. The dry composition may shipped, for example, in a vial, ampoule, sachette, syringe, catheter, or other container, and it may be mixed with an appropriate liquid carrier (e.g. sterile water for injection, physiological saline, phosphate buffer, a solution containing an imaging contrast agent, etc.) prior to administration. In this way the concentration of the composition to be injected may be varied at will, depending on the specific application at hand, as desired by the health care practitioner in charge of the procedure. One or more containers of liquid carrier may also be supplied in a vial or other container and shipped, along with the dry particles, in the form of a kit.

The injectable particles may also be stored in a suspension that contains water in addition to the particles themselves, as well as other optional agents such as one or more of the tonicity adjusting agents, therapeutic agents, suspension agents, contrast media, and pH adjusting agents listed above, among others. The suspension may be stored, for example, in a vial, ampoule, sachette, syringe, catheter, or other container. The suspension may also be mixed with an appropriate liquid carrier (e.g. sterile water for injection, physiological saline, phosphate buffer, a solution containing contrast agent, etc.) prior to administration, allowing the concentration of administered particles (as well as other optional agents) in the suspension to be reduced prior to injection, if so desired by the health care practitioner in charge of the procedure. One or more containers of liquid carrier may also be supplied in a vial or other container to form a kit.

The amount of injectable particles within a suspension to be injected may be determined by one skilled in the art. The amount of particles may be limited by the fact that when the amount of particles in the composition is too low, too much liquid may be injected, possibly allowing particles to stray far from the site of injection, which may result in undesired embolization or bulking of vital organs and tissues. When the amount of particles is too great, the delivery device (e.g., catheter, syringe, etc.) may become clogged.

In certain embodiments, the density of the aqueous phase that suspends the particles is close to that of the particles themselves, thereby promoting an even suspension. The density of the aqueous phase may be increased, for example, by increasing the amount of solutes that are dissolved in the aqueous phase, and vice versa.

As noted above, permanent or temporary occlusion of blood vessels is essential for managing various diseases, disorders and conditions. For example, fibroids, also known as leiomyoma, leiomyomata or fibromyoma, are the most common benign tumors of the uterus. These non-cancerous growths are present in significant fraction of women over the age of 35. In most cases, multiple fibroids are present, often up to 50 or more. Fibroids can grow, for example, within the uterine wall ("intramural" type), on the outside of the uterus ("subserosal" type), inside the uterine cavity ("submucosal" type), between the layers of broad ligament supporting the uterus ("interligamentous" type), attached to another organ ("parasitic" type), or on a mushroom-like stalk ("pedunculated" type). Fibroids may range widely in size, for example, from a few millimeters to 40 centimeters. In some women, fibroids can become enlarged and cause excessive bleeding and pain. While fibroids have been treated by surgical removal of the fibroids (myomectomy) or by removal of the uterus (hysterectomy), recent advances in uterine embolization now offer a nonsurgical treatment. Thus, injectable compositions in accordance with the present invention can be used to treat uterine fibroids.

Methods for treatment of fibroids by embolization are well known to those skilled in the art (see, e.g., Pub. No. US 2003/0206864 to Mangin and the references cited therein). Uterine embolization is aimed at starving fibroids of nutrients. Numerous branches of the uterine artery may supply uterine fibroids. In the treatment of fibroids, embolization of the entire uterine arterial distribution network is often preferred. This is because it is difficult to selectively catheterize individual vessels supplying only fibroids, the major reason being that there are too many branches for catheterization and embolization to be performed in an efficient and timely manner. Also, it is difficult to tell whether any one vessel supplies fibroids rather than normal myometrium. In many women, the fibroids of the uterus are diffuse, and embolization of the entire uterine arterial distribution affords a global treatment for every fibroid in the uterus.

In a typical procedure, a catheter is inserted near the uterine artery by the physician (e.g., with the assistance of a guide wire). Once the catheter is in place, the guide wire is removed and contrast agent is injected into the uterine artery. The patient is then subjected to fluoroscopy or X-rays. In order to create an occlusion, an embolic agent is introduced into the uterine artery via catheter. The embolic agent is carried by the blood flow in the uterine artery to the vessels that supply the fibroid. The particles flow into these vessels and clog them, thus disrupting the blood supply to the fibroid. In order for the physician to view and follow the occlusion process, contrast agent may be injected subsequent to infusion of the embolic agent.

Controlled, selective obliteration of the blood supply to tumors is also used in treating solid tumors such as renal carcinoma, bone tumor and liver cancer, among various others. The idea behind this treatment is that preferential blood flow toward a tumor will carry the embolization agent to the tumor thereby blocking the flow of blood which supplies nutrients to the tumor, thus, causing it to shrink. Embolization may be conducted as an enhancement to chemotherapy or radiation therapy.

Particle compositions in accordance with the invention may also be used to treat various other diseases, conditions and disorders, including treatment of the following: arteriovenous fistulas and malformations including, for example, aneurysms such as neurovascular and aortic aneurysms, pulmonary artery pseudoaneurysms, intracerebral arteriovenous fistula, cavernous sinus dural arteriovenous fistula and arterioportal fistula, chronic venous insufficiency, varicocele, pelvic congestion syndrome, gastrointestinal bleeding, renal bleeding, urinary bleeding, varicose bleeding, uterine hemorrhage, and severe bleeding from the nose (epistaxis), as well as preoperative embolization (to reduce the amount of bleeding during a surgical procedure) and occlusion of saphenous vein side branches in a saphenous bypass graft procedure, among other uses.

Particle compositions in accordance with the invention may also be used in tissue bulking applications, for example, as augmentative materials in the treatment of urinary incontinence, vesicourethral reflux, fecal incontinence, intrinsic sphincter deficiency (ISD) or gastro-esophageal reflux disease, or as augmentative materials for aesthetic improvement. For instance, a common method for treating patients with urinary incontinence is via periurethral or transperineal injection of a bulking material. In this regard, methods of injecting bulking agents commonly require the placement of a needle at a treatment region, for example, periurethrally or transperineally. The bulking agent is injected into a plurality of locations, assisted by visual aids, causing the urethral lining to coapt. In some cases, additional applications of bulking agent may be required.

The particle compositions of the invention may also be used to deliver one or more therapeutic agents locally in order to treat any of a number of diseases, disorders and conditions treatable by local drug delivery.

The precise dose of the particulate composition of the present invention to be employed will depend on the nature of the disease, disorder or condition being treated, the particular type and size of the particles used, and the mode of administration, among other factors, and should be decided according to the judgment of the practitioner and each subject's circumstances according to acceptable clinical procedure. An effective amount is, for example, (a) an amount sufficient to produce an occlusion or emboli at a desired site in the body, (b) an amount sufficient to achieve the degree of bulking desired (e.g., an amount sufficient to improve urinary incontinence, vesicourethral reflux, fecal incontinence, ISD or gastro-esophageal reflux, or an amount sufficient for aesthetic improvement), or (c) an amount sufficient to locally treat a disease, disorder or condition. Effective doses may also be extrapolated from dose-response curves derived from animal model test systems, among other techniques. Subjects include vertebrate subjects, particularly humans and various animals including pets and livestock.

The present invention encompasses various ways of administering the particulate compositions of the invention to effect embolization, bulking or therapeutic agent release. One skilled in the art can determine the most desirable way of administering the particles depending on the type of treatment and the condition of the patient, among other factors. Methods of administration include, for example, percutaneous techniques as well as other effective routes of administration. For example, the particulate compositions of the invention may be delivered through a syringe or through a catheter, for instance, a FasTracker® microcatheter (Boston Scientific, Natick, Mass., USA), which can be advanced over a guidewire, a steerable microcatheter, or a flow-directed microcatheter (MAGIC, Balt, Montomorency, France).

Various aspects of the invention of the invention relating to the above are enumerated in the following paragraphs:

Aspect 1. An injectable medical composition comprising multicomponent particles in an aqueous suspension, wherein the multicomponent particles comprise a first polymeric component that comprises a first polymer and a second polymeric component that comprises a second polymer, and wherein the second polymer differs from the first polymer.

Aspect 2. The injectable medical composition of Aspect 1, comprising spherical multicomponent particles.

Aspect 3. The injectable medical composition of Aspect 1, comprising spherical multicomponent particles in which the first and second components of the spherical multicomponent particles do not correspond to a core and a shell and in which the first and second components of the spherical particles do not correspond to concentric shells.

Aspect 4. The injectable medical composition of Aspect 1, comprising spherical multicomponent particles that have at least one plane of asymmetry passing through their centers.

Aspect 5. The injectable medical composition of Aspect 1, comprising multicomponent particles that comprise multiple cores that correspond to the first polymeric component separated from one another by the second polymeric component.

Aspect 6. The injectable medical composition of Aspect 1, comprising multicomponent particles that comprise multiple discrete surface regions that correspond to the first polymeric component separated from one another by the second polymeric component.

Aspect 7. The injectable medical composition of Aspect 1, comprising multicomponent particles in which the first and second polymeric components are in a side by side arrangement.

Aspect 8. The injectable medical composition of Aspect 1, comprising spherical multicomponent particles in which the first and second polymeric components are hemispheres.

Aspect 9. The injectable medical composition of Aspect 1, comprising a multicomponent particle formed by a process that comprises (a) contacting one or more first liquid droplets comprising said first polymer or a precursor thereof with one or more second liquid droplets comprising said second polymer or a precursor thereof such that the first and second liquid droplets coalesce into a single composite droplet, and (b) solidifying the single composite droplet to form said particle.

Aspect 10. The injectable medical composition of Aspect 1, wherein 95 vol % of the particles have a longest linear cross-sectional dimension between 40 μm and 5000 μm.

Aspect 11. The injectable medical composition of Aspect 1, wherein the particles are spherical and wherein 95 vol % of the particles have a diameter between 40 μm and 5000 μm.

Aspect 12. The injectable medical composition of Aspect 1, wherein the first polymeric component comprises a first therapeutic agent.

Aspect 13. The injectable medical composition of Aspect 12, wherein the second polymeric component comprises the first therapeutic agent.

Aspect 14. The injectable medical composition of Aspect 13, wherein the first and second polymers are biodegradable and have differing rates of biodegradation.

Aspect 15. The injectable medical composition of Aspect 12, wherein the second polymeric component comprises a second therapeutic agent that differs from the first therapeutic agent.

Aspect 16. The injectable medical composition of Aspect 15, wherein the first and second polymers are biodegradable and have differing rates of biodegradation.

Aspect 17. The injectable medical composition of Aspect 1, wherein the first and second polymers are biodegradable and have differing rates of biodegradation.

Aspect 18. The injectable medical composition of Aspect 1, wherein the first and second polymers are biostable Aspect 19. The injectable medical composition of Aspect 1, wherein the first polymer is biostable and the second polymer is biodegradable.

Aspect 20. The injectable medical composition of Aspect 1, wherein the first polymeric component is a hydrogel.

Aspect 21. The injectable medical composition of Aspect 20, wherein the second polymeric component comprises a therapeutic agent.

Aspect 22. The injectable medical composition of Aspect 1, wherein the first polymer is an ionic polymer.

Aspect 23. The injectable medical composition of Aspect 22, wherein the second polymer is an ionic polymer.

Aspect 24. The injectable medical composition of Aspect 22, wherein the first polymeric component comprises a therapeutic agent.

Aspect 25. The injectable medical composition of Aspect 1, wherein the overall density of the particles matches that of the aqueous phase within which they are suspended.

Aspect 26. The injectable medical composition of Aspect 1, wherein the injectable medical composition comprises a tonicity adjusting agent.

Aspect 27. The injectable medical composition of Aspect 1, wherein the tonicity adjusting agent is selected from sugars, polyhydric alcohols, inorganic salts and combinations thereof.

Aspect 28. The injectable medical composition of Aspect 1, wherein the injectable medical composition is within a glass container or a preloaded syringe.

Although various aspects and embodiments are specifically illustrated and described herein, it will be appreciated that modifications and variations of the present invention are covered by the above teachings and are within the purview of any appended claims without departing from the spirit and intended scope of the invention.

What is claimed is:

1. An injectable medical composition comprising multicomponent particles in an aqueous suspension, wherein the multicomponent particles comprise a first polymeric component that comprises a first ionic polymer and a second polymeric component that comprises a second ionic polymer, wherein the second polymer is of opposite charge to the first polymer, and wherein said multicomponent particles comprise multiple discrete surface regions of the first polymeric component that are separated from one another by a single continuous phase of the second polymeric component.

2. The injectable medical composition of claim 1, wherein the multicomponent particles are spherical multicomponent particles.

3. The injectable medical composition of claim 1, comprising a multicomponent particle formed by a process that comprises (a) contacting one or more first liquid droplets comprising said first polymer or a precursor thereof with one or more second liquid droplets comprising said second polymer or a precursor thereof such that the first and second liquid droplets coalesce into a single composite droplet, and (b) solidifying the single composite droplet to form said particle.

4. The injectable medical composition of claim 1, wherein 95 vol % of said particles have a longest linear cross-sectional dimension between 40 µm and 5000 µm.

5. The injectable medical composition of claim 1, wherein said particles are spherical and wherein 95 vol % of said particles have a diameter between 40 µm and 5000 µm.

6. The injectable medical composition of claim 1, wherein said first polymeric component comprises a first therapeutic agent.

7. The injectable medical composition of claim 6, wherein said second polymeric component comprises said first therapeutic agent.

8. The injectable medical composition of claim 7, wherein said first and second polymers are biodegradable and have differing rates of biodegradation.

9. The injectable medical composition of claim 6, wherein said second polymeric component comprises a second therapeutic agent that differs from said first therapeutic agent.

10. The injectable medical composition of claim 9, wherein said first and second polymers are biodegradable and have differing rates of biodegradation.

11. The injectable medical composition of claim 1, wherein said first and second polymers are biodegradable and have differing rates of biodegradation.

12. The injectable medical composition of claim 1, wherein said first polymeric component is a hydrogel.

13. The injectable medical composition of claim 12, wherein said second polymeric component comprises a therapeutic agent.

14. The injectable medical composition of claim 1, wherein the overall density of said particles matches that of an aqueous phase within which they are suspended.

15. The injectable medical composition of claim 1, wherein said injectable medical composition comprises a tonicity adjusting agent.

16. The injectable medical composition of claim 1, wherein said tonicity adjusting agent is selected from sugars, polyhydric alcohols, inorganic salts and combinations thereof.

17. The injectable medical composition of claim 1, wherein said injectable medical composition is within a glass container or a preloaded syringe.

18. The injectable medical composition of claim 1, wherein said first and second polymers are biostable.

19. The injectable medical composition of claim 1, wherein said first polymer is biostable and said second polymer is biodegradable.

20. The injectable medical composition of claim 1, wherein said first polymeric component comprises a first therapeutic agent and wherein either (a) said first polymer is biodegradable and said second polymer is biostable or (b) said first and second polymers are biodegradable and have differing rates of biodegradation.

* * * * *